United States Patent [19]

Kaplan et al.

[11] Patent Number: 5,426,046
[45] Date of Patent: Jun. 20, 1995

[54] HUMAN MONOCLONAL ANTIBODY TO LIPID A OF GRAM NEGATIVE BACTERIA

[75] Inventors: Henry S. Kaplan, Stanford; Abraham I. Braude, La Jolla; Nelson N. H. Teng, Hillsborough, all of Calif.

[73] Assignee: The Board of Trustees of the Leland Stanford Junior University, Stanford, Calif.

[21] Appl. No.: 112,048

[22] Filed: Aug. 25, 1993

Related U.S. Application Data

[63] Continuation of Ser. No. 792,815, Nov. 15, 1991, abandoned, which is a continuation of Ser. No. 546,401, Jun. 29, 1990, abandoned, which is a continuation of Ser. No. 885,223, Jul. 14, 1986, abandoned, which is a continuation of Ser. No. 550,264, Nov. 8, 1983, abandoned.

[51] Int. Cl.$^6$ ............... C12N 5/12; C07K 16/12
[52] U.S. Cl. ............... 435/240.27; 530/388.4; 530/388.2; 530/388.15
[58] Field of Search ............... 424/85.8; 530/388.4, 530/388.2, 388.15; 435/240.27, 70.21

[56] References Cited

U.S. PATENT DOCUMENTS 5,057,598 10/1991 Pollack et al. ............... 530/387

OTHER PUBLICATIONS

Ziegler et al., The New England Journal of Medicine, vol. 307(20), pp. 1225–1230, Nov. 11, 1982.
Sevier, et al., Clin. Chem., 27(11):1797–1806, 1981.
Dunn et al., Surgery, 92:212–9, 1982.
Ziegler et al., Trans. Assoc. Amer. Phys., 91:253–8, 1978.
Waldmann, T. A., Science, 252:1657–1662, Jun. 21, 1991.
Spalding, B. J., Bio technology, 11:428–429, Apr. 1993.
Sloan, A., The Washington Post, p. D3, Jan. 19, 1993.
Stone, R., Science, 259:1243, Feb. 26, 1993.
Wenzel, R. P., New England Journal of Med, 326(17):1151–1152, Apr. 23, 1992.
Warren et al., New Engl. Journal of Med, 326(17):1153–1157, Apr. 23, 1992.

Primary Examiner—David L. Lacey
Assistant Examiner—Susan A. Loring
Attorney, Agent, or Firm—Colley Godward Castro Huddleson & Tatum

[57] ABSTRACT

A human monoclonal antibody, C5, specific for lipid A of the endotoxin core of Gram-negative bacteria and the hybridoma cell line which produces the antibody. The monoclonal antibody is produced by the fusion of lipid A sensitized lymphocytes and an appropriate fusion partner.

2 Claims, No Drawings

HUMAN MONOCLONAL ANTIBODY TO LIPID A OF GRAM NEGATIVE BACTERIA

CROSS REFERENCE TO RELATED APPLICATIONS

This application is a continuation of U.S. application Ser. No. 07/792,815, filed Nov. 15, 1991, now abandoned, which is a continuation of U.S. Application Ser. No. 07/546,401, filed Jun. 29, 1990, now abandoned, which is a continuation of U.S. Application Ser. No. 06,885,223, filed Jul. 14, 1986, now abandoned, which is a continuation of U.S. Application Ser. No. 06/550,264, filed Nov. 8, 1983, now abandoned.

BACKGROUND

Gram-negative sepsis is a very common type of bacterial infection, particularly in burn victims and in patients treated with high doses of cancer chemotherapeutic agents for leukemia or other forms of cancer. There are several reasons for postulating that lipopolysaccharide, or endotoxin, in the cell wall of invading Gram-negative bacteria is an important factor in mortality. Despite the use of potent antibiotics and aggressive support techniques, there is still a high frequency of death.

Lipopolysaccharide has three portions: the oligosaccharide side chains; the core polysaccharide; and lipid A, which is considered to be the toxic moiety. Antibody to complete polysaccharide is directed primarily against the side chains, which differ widely from strain to strain. Therefore, antiserum to a complete polysaccharide is less likely to have protective activity against a broad range of bacterial strains. However, there is much less strain variation in lipid A than in the side chains. The core regions of most Gram-negative bacteria contain similar lipid A units. Antibodies to the core structure should, therefore, provide a broader scope of protection.

RELEVANT LITERATURE

Ziegler et al., *N.E.J. of Medicine* (1982) 307:1225–1230 report the preparation of polyclonal antiserum to the J5 mutant of *E. coli* 0111:B4, a mutant which produces a lipopolysaccharide consisting solely of core determinants.

U.S. Patent application Ser. No. 457,795, filed Jan. 13, 1983, now U.S. Pat. No. 4,574,116, describes the preparation of heteromyeloma cells and the deposit of an exemplary heteromyeloma at the A.T.C.C., Rockville, Md. given Accession No. CRL8192.

SUMMARY OF THE INVENTION

Human monoclonal antibodies are produced against lipid A from a Gram-negative bacterium to provide human monoclonal antibodies useful for passive immunization against Gram-negative bacteremia. The monoclonal antibodies are achieved by fusion of lipid A sensitized lymphocytes with an appropriate fusion partner to produce a hybridoma which provides for the stable secretion of an immunoglobulin specific for the bacterial endotoxin.

DESCRIPTION OF THE SPECIFIC EMBODIMENTS

Methods are provided for the production of and the use of human monoclonal antibodies specific for a broad range of Gram-negative endotoxins. The human monoclonal antibodies may be administered for passive immunization to a host susceptible to Gram-negative bacteremia. The monoclonal antibodies react with a wide range of Gram-negative bacterial strains, because the monoclonal antibodies are prepared against lipid A, which tends to be relatively conserved, as distinct from the side chains of the endotoxin.

The subject monoclonal antibodies are obtained by employing human lymphocytes which have been sensitized with lipid A from a Gram-negative bacterium. Particularly, the J5 mutant of *E. coli* 0111:B4 provides a lipopolysaccharide consisting solely of the core determinants. A human host may be sensitized with J5 vaccine prepared from *E. coli* J5 bacterial cells as described in Ziegler, supra. Desirably, patients are chosen who are intended for a splenectomy, where the spleen will be removed shortly after the immunization program. The vaccine may be used by itself or in conjunction with adjuvants to enhance the immune response. Conveniently, the host may be immunized subcutaneously at one or more sites with injections of about 0.5 to 2 ml, usually about 1 ml, where the vaccine will induce a hemagglutinating antibody titer in the range of about 1:32 to 1:256. One or more booster vaccinations may be given, generally not more than about two booster vaccinations, where the vaccinations may be separated by from about 48 hr to about three weeks.

Where splenocytes are to be employed for the fusion, the spleen will normally be removed from about 2 to 21 days after the final vaccination. The spleen is removed and the T-cells separated by any convenient technique, e.g., mass E-rosetting. Desirably, the B-lymphocytes will be transformed with Epstein-Barr virus (EBV) to generate immortalized lymphoblastoid cells, which can be used in the subsequent fusion with a fusion partner.

A wide variety of fusion partners may be employed which provide for the secretion of human immunoglobulins. Desirably, the immunoglobulin which is secreted will be IgM, although IgG or IgA may also find use. The production of IgD and IgE is uncommon. The fusion partner may be a mouse myeloma line, a heteromyeloma line (see Application Ser. No. 457,795, U.S. Pat. No. 4,574,116, or a human myeloma or other immortalized line, as described in PCT Application No. 81/00957, Schlom et al., *PNAS USA* (1980) 77:6841–6845; and Croce et al., *Nature* (1980) 288:488–489.

Desirable characteristics of a fusion partner are high efficiency of fusion to provide for a high proportion of immunoglobulin-producing hybridomas, absence of the production of individual chains or immunoglobulins unassociated with the immunoglobulin of interest, and the maintenance of the capability of continuously secreting the desired immunoglobulin over long periods of time. Illustrative fusion partners include the mouse myeloma cell lines X63-Ag8.653, P3-NS1/1Ag4 and S194/5.XXO.BU1; human fusion partners, such as UC729-6 and SKO-007; and mouse-human heteromyeloma lines, such as SHM-A6 and SHM-D33. The fusion is carried out in the presence of a non-ionic detergent, normally polyethylene glycol, for a short period of time, the detergent removed, and the cells subjected to selective conditions which are cytotoxic to the parent cells, but not to fused hybrid cells, e.g. HAT, HAT and ouabain, etc.

Variations in the B-lymphocyte preparation for fusion include the use of unseparated versus B-cell-enriched spleen cells, mitogen-stimulated versus unstimulated cells, and the like. The particular technique will vary depending upon the success which is achieved with the fusion.

Hybrid cells which grow out from the selective media are seeded in individual wells and their supernatants screened by any convenient technique for the monoclonal antibodies of interest. Cells showing the presence of the monoclonal antibodies of interest are then cloned by limiting dilution procedures and the clones producing the highest level of specific antibody expanded. The antibodies may then be further characterized as to classes, subclasses and type.

The antibodies may be purified by any convenient technique, such as chromatography, electrophoresis, precipitation and extraction, or the like.

The antibodies may be employed without further change after purification or may be modified by reduction to various sized fragments, such as F(ab')$_2$·Fab, Fv, or the like. Alternatively, the antibodies may be labeled with various agents, such as cytotoxic agents, e.g. the A chain of ricin or diphtheria toxin, antibiotics, or the like. Particularly, the IgG complement fixing subclasses, e.g. IgG3, may be employed for lysis of bacterial cells.

The hybridomas may find use other than for production of the immunoglobulin. The hybridomas may be fused with other cells to transfer the genes providing for expression of the immunoglobulin, thus providing new hybridomas. The hybridomas may be used as a source for the DNA or mRNA encoding for the rearranged, activated immunoglobulin genes, which may be isolated, cloned by recombinant DNA techniques and transferred to other cells for the production of the specific immunoglobulin. Particularly, by isolating rearranged DNA or by preparing cDNA from messenger RNA a sequence may be obtained free of introns.

For use in passive immunization, the antibodies may be infused or injected into a patient. Amounts of the antibodies employed for immunization will vary, generally being in the range of about 0.005 to 0.05 ml/kg of the immunoglobulin.

The following examples are offered by way of illustration and not by way of limitation.

EXPERIMENTAL

Patient D. M. received one injection of J5 vaccine about two weeks prior to staging laparotomy with splenectomy. The spleen cells were suspended and aliquots prepared as unfractionated preparations containing both T- and B-cells; B-cell-enriched populations from which T-cells had been depleted by mass E-rosetting; and on the following day, a population of B-cells was infected with B95-8 strain of EBV to generate immortalized lymphoblastoid cells (Brown and Miller, *J. Immunol.* (1982) 128:24-29).

The first fusion with the spleen cells of patient D. M. employed unstimulated B-cells and SHM-D33 in a 1:4 ratio. The cell fusion employed was the method described by Oi and Herzenberg (1979) In: *Selected Methods in Cellular Immunology* (B. B. Mishell and S. M. Shiigi, eds.) San Francisco: W. J. Freeman Publishers, pp. 351-372, modified as follows. The heteromyeloma cells ($1 \times 10^7$) and lymphocytes ($4 \times 10^7$) (see Application Ser. No. 457,795) were each washed twice with 50 ml calcium- and magnesium-free PBS (PBS-CMF) (Schneiderman et al., *Somatic Cell Genetics* (1979) 5:263-269). The cells were then mixed, washed with 10 ml PBS-CMF, and 1 ml of 40% (w/v) polyethylene glycol 1540 (A.T.C.C.) in PBS-CMF was added to the pellet with gentle stirring for 1 min. After one more minute, 1 ml of Iscove's medium (without fetal calf serum) was added in 1 min with gentle stirring. Another ml of medium was added at the same rate. Then 8 ml of Iscove's medium (without fetal calf serum) was added at 2 ml/min. The final pellet was resuspended in selection medium and added to 96-well plates at a concentration of $2 \times 10^5$ cells/well; mouse thymocytes were used as feeders at $10^6$/ well. Selection was carried out in HAT medium (Littlefield, *Science* (1964) 145:709-710 and $5 \times 10^{-7}$M ouabain.

By 11 days, 23 viable hybrids had been obtained from 170 wells which had been seeded. Fourteen days later it was found that clone 2G7 was positive for secretion of specific anti-J5 antibody by an ELISA test. The ELISA procedure is as described in Engvall, *Med. Biol.* (1977) 55:193-200 using peroxidase-conjugated goat anti-human IgM and IgG (Tago, Burlingame, Calif.) as secondary antibodies and 2,2-azino-di-(3-ethylbenzthiazoline) sulfonic acid as the substrate. The J5 endotoxin was used at a concentration of 100-200 $\mu$g/ml to coat the plates for ELISA (Linbro E.I.A. plates were used for immunoglobulin assays and Dynatech polyvinyl plates for anti-J5 antibodies). However, this clone lost viability and died out, although by 38 days later, 24 of 29 clones were still producing human Ig but none was specific for reactivity with J5 endotoxin.

In a second set of fusions, EBV-transformed lymphoblastoid cells were fused with the following heteromyeloma cell lines: SHM-D29, -D-33 (G3), -D36 (G7), -D39, -D49, -D42, -D70, -A6 (H4) and with the parental mouse myeloma line, X63-Ag8,653 ("653"). Assays 22 days later revealed that the best producers stem from fusions with SHM-A6 (H4): 58/120 wells; SHM-D3 (G3): 38/112 wells; and 653 cells: 78/120 wells. By 14 days later, repeat tests revealed Ig production was 100% for subclones of viable hybrids derived from fusion with SHM-D33, 92% for those derived from fusion with 653, and 77% for those derived from fusion with A6. Meanwhile, subcloning of the producer clones had been carried out and testing of these revealed that subclones 2G5 and 1E8 derived from the fusion with SHM-D33 (G3); 1F10, 1C2 and 2G9 derived from the fusion with SHM-A6 (H4); and 1B7, 1E3, 1G1, 2F9, 2E6 and 2D7 derived from the fusion with 653 cells were specific anti-J5 endotoxin antibody producers. These subclones were retested some 18 days later and found to react specifically not only with J5 endotoxin, but with the complete endotoxin (LPS) molecules derived from another strain of *E. coli* (055:B5). A total of nine clones have stably produced human monoclonal antibodies against J5 for over three months.

Supernatant fluids were isolated from a number of the clones and used for testing. In vitro tests have confirmed that these human monoclonal antibodies react not only with lipid A from *E. coli* but also with lipid A from several other Gram-negative bacterial species, and in vivo tests have demonstrated striking protection of mice against lethal sepsis induced by *Pseudomonas aeruginosa* and *E. coli* 0111B4. No fever was noted when these human monoclonal antibodies were tested for pyrogenicity by intravenous injection in rabbits.

The subject monoclonal antibodies are specific for lipid A from Gram-negative bacteria, so as to be generally useful for passive immunization against and treatment of Gram-negative bacteremia and endoctoxic shock. The monoclonal antibodies are highly specific, having a high binding constant.

The ability to maintain the stable production of a specific monoclonal antibody whose characteristics can be defined is extremely important. First, the subject hybridomas can be expanded so as to provide continuous production of human monoclonal anti-J5 antibodies in useful amounts for general application. Secondly, because the subject monoclonal antibodies can be uniformly produced, they can be characterized to ensure adequate purification. Thirdly, because the monoclonal antibodies are human, any immune response upon repeated rejection should be relatively low and not hazard the health and continued viability of the host. Fourth, information can be developed by experience with the subject monoclonal antibodies concerning a host response to the same or different idiotypes having the same binding specificity.

The hybridoma C5(1F10) was deposited at the American Type Culture Collection, 12301 Parklawn Drive, Rockville, Md. 20852, on Jan. 5, 1984 and given Accession No. HB8669.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A hybridoma from an immortalized cell line and a human B-lymphocyte sensitized to J5 endotoxin, wherein said hybridoma is cell line C5, said cell line deposited with the ATCC as deposit No. HB8669.

2. A human monoclonal antibody which specifically binds to lipid A of Gram-negative bacteria, wherein said antibody is produced by hybridoma cell line C5, said cell line deposited with the ATCC as deposit No. HB8669.

* * * * *